(12) United States Patent
Brewer et al.

(10) Patent No.: US 7,003,348 B1
(45) Date of Patent: Feb. 21, 2006

(54) MONITORING CARDIAC GEOMETRY FOR DIAGNOSTICS AND THERAPY

(75) Inventors: James E. Brewer, Lino Lakes, MN (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 247 days.

(21) Appl. No.: 10/612,611

(22) Filed: Jul. 1, 2003

(51) Int. Cl.
A61N 1/18 (2006.01)

(52) U.S. Cl. .......................................... 607/17; 600/508
(58) Field of Classification Search ................. 607/24, 607/17; 600/508, 527
See application file for complete search history.

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,940,052 A | 7/1990 | Mann et al. | 128/419 |
| 4,944,298 A | 7/1990 | Sholder | 128/419 PG |
| 5,178,149 A | 1/1993 | Imburgia et al. | 128/662.06 |
| 5,417,715 A | 5/1995 | Noren et al. | 607/9 |
| 5,476,483 A | 12/1995 | Bornzin et al. | 607/17 |
| 5,480,412 A * | 1/1996 | Mouchawar et al. | 607/6 |
| 5,549,650 A * | 8/1996 | Bornzin et al. | 607/24 |
| 5,738,096 A | 4/1998 | Ben-Haim | 128/653.1 |
| 6,009,349 A * | 12/1999 | Mouchawar et al. | 607/6 |
| 6,066,094 A | 5/2000 | Ben-Haim | 600/437 |
| 6,077,236 A | 6/2000 | Cunningham | 600/587 |
| 6,129,744 A | 10/2000 | Boute | 607/25 |
| 6,278,894 B1 | 8/2001 | Salo et al. | 600/547 |
| 6,285,898 B1 | 9/2001 | Ben-Haim | 600/374 |
| 6,336,903 B1 | 1/2002 | Bardy | 600/508 |
| 6,421,565 B1 | 7/2002 | Hemmingsson | 607/17 |
| 2002/0002389 A1 | 1/2002 | Bradley et al. | 607/8 |
| 2002/0087089 A1 | 7/2002 | Ben-Haim | 600/509 |
| 2002/0115939 A1 | 8/2002 | Mulligan et al. | 600/510 |

FOREIGN PATENT DOCUMENTS

| | | |
|---|---|---|
| WO | WO 99/07285 | 2/1999 |
| WO | WO 01/87410 A2 | 11/2001 |
| WO | WO 01/87410 A3 | 11/2001 |
| WO | WO 02/053228 | 7/2002 |

OTHER PUBLICATIONS

Shier, D., Hole, J., Butler, J., Lewis, R., Hole's Human Anatomy & Physiology. New York: McGraw-Hill, 2002, (9th edition), pp. 591-593.*

Schussheim et al., Midwall fractional shortening is an independent predictor of left ventricular diastolic dysfunction in asymptomatic patients with systemic hypertension. American Journal of Cardiology. Nov. 1, 1998; 82(9):1056-9.*

Zugck et al., Risk stratification in middle-aged patients with congestive heart failure: prospective comparison of the Heart Failure Survival Score (HFSS) and a simplified two-variable model. The European Journal of Heart Failure. 2001(3) 577-585.□□.*

Silva, Carlos Eduardo Suaide, "*Study of the Myocardial Contraction and Relaxation Velocities through Douppler Tissue Imaging Echocardiography. A New Alternative in the Assessment of the Segmental Ventricular Function,*" Arq Bras Cardiol, vol. 78, No. 2, 206-11 (2002).

(Continued)

Primary Examiner—Jeffrey R. Jastrzab
Assistant Examiner—Alyssa M. Alter

(57) ABSTRACT

An exemplary method includes determining, in vivo, position, displacement and/or spatial time derivatives of myocardial tissue. Such determinations are optionally made with respect to systolic and/or diastolic cycles. Further, position, displacement and/or spatial time derivatives may be used in cardiac diagnosis or therapy. Other exemplary methods, devices and/or systems are also disclosed.

22 Claims, 15 Drawing Sheets

OTHER PUBLICATIONS

Zugck, Christian et al., "*Risk Stratification in Middle-aged Patients with Congestive Heart Failure: Prospective Comparison of the Heart Failure Survival Score (HFSS) and a Simplified Two-Variable Model*," The European Journal of Heart Failure (3) (2001), pp 577-585.

Beringer, Jacqueline et al., "*A Unifying Representation of Ventricular Volumetric Indexes*," IEEE Transactions on Biomedical Engineering, vol. 45, No. 3, Mar. 1998, pp 365-371.

* cited by examiner

POLYNOMIAL MODEL
$$Y = C_0 + C_1 \cdot X + C_2 \cdot X^2 + C_3 \cdot X^3$$

LINEAR MODEL
$$Y = C_0 + C_1 \cdot X$$
$$C_1 = M = \Delta D/\Delta V = \Delta D'/\Delta V'$$

OTHER MODEL
$$Y = F(X) \text{ AND/OR OTHER PARAMETER}$$

MONITORING CARDIAC GEOMETRY FOR DIAGNOSTICS AND THERAPY

CROSS REFERENCE TO RELATED APPLICATIONS

The present application is related to copending U.S. patent application Ser. No. 10/612,770, filed concurrently herewith, titled "System and Method for Determining Cardiac Geometry," which is incorporated herein by reference.

TECHNICAL FIELD

The present invention generally relates to devices, systems and/or methods for providing cardiac pacing therapy. More particularly, various exemplary methods determine one or more parameters related to cardiac geometry and use such information for diagnostics and/or therapy.

BACKGROUND

Congestive heart failure (CHF) is a condition that is often associated with a weakened heart that cannot pump enough blood to body organs. For example, as pumping action is lost, blood may back up into the heart and other areas of the body, including the liver, gastrointestinal tract, extremities and/or lungs. While implantable cardiac therapy devices are often used to overcome deleterious effects caused by CHF, such devices cannot halt progress of CHF. However, some implantable cardiac devices can be programmed to compensate for worsening stages of CHF. For example, as CHF progresses, the myocardium weakens, which typically results in an increased left ventricular volume. To compensate for the increase in volume, a clinician may periodically measure a patient's left ventricular diameter, or another parameter associated with cardiac geometry, and program the implanted cardiac therapy device accordingly. This technique, however, requires clinical intervention, which consumes time and resources. Reliable exemplary devices, methods and/or systems for determining cardiac geometry using an implanted cardiac therapy device optionally overcome such limitations and are presented herein.

SUMMARY

An exemplary method includes determining, in vivo, position, displacement and/or spatial time derivatives of myocardial tissue. Such determinations are optionally made with respect to systolic and/or diastolic cycles. Further, position, displacement and/or spatial time derivatives may be used in cardiac diagnosis or therapy. Other exemplary methods, devices and/or systems are also disclosed.

The various exemplary methods, devices and/or systems described herein, and equivalents thereof (e.g., structural and/or functional), are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are intended to be implemented in connection with any stimulation device that is configured or configurable to generate a potential field, sense a potential, and/or stimulate or shock a patient's tissue (e.g., cardiac, nerve, muscle, etc.).

Figure 1:
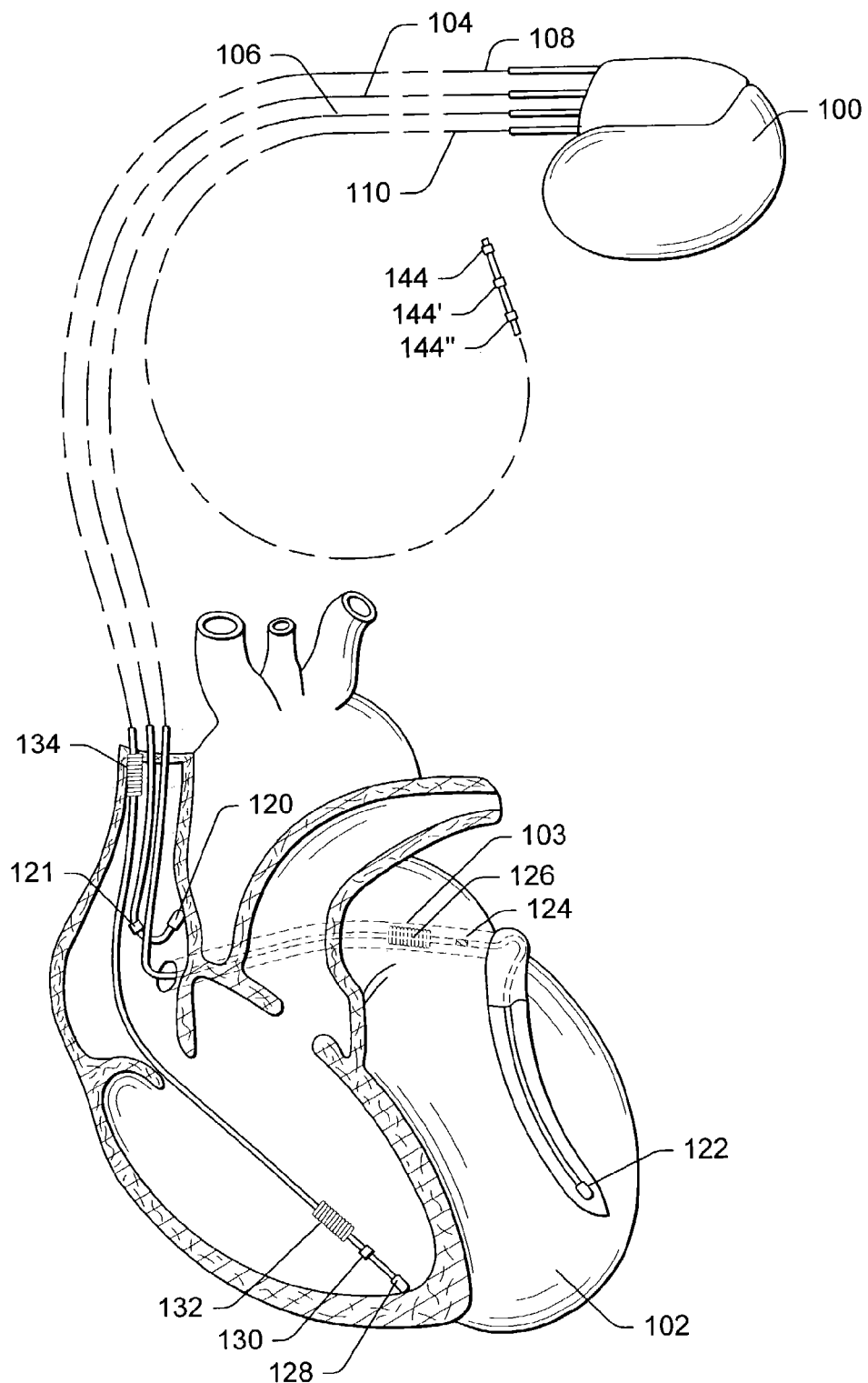
FIG. 1 is a simplified diagram illustrating an implantable stimulation device in electrical communication with at least three leads implanted into a patient's heart for generating potential fields, sensing potentials, and delivering multi-chamber stimulation and shock therapy.

FIG. 1 shows an exemplary stimulation device 100 in electrical communication with a patient's heart 102 by way of three leads 104, 106, 108, suitable for generating potential fields, sensing potentials, and/or delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for generation of potential fields, sensing potentials and/or stimulation of tissue (e.g., cardiac, nerve, muscle, etc.). The exemplary lead 110 may be positioned, for example, in and/or near a patient's heart or near an autonomic nerve within a patient's body and remote from the heart. The right atrial lead 104, as the name implies, is positioned in and/or passes through a patient's right atrium. The right atrial lead 104 optionally generates a potential field (e.g., in combination with another electrode), senses atrial cardiac signals or other signals and/or provides right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well.

To generate a potential field; sense potentials, atrial cardiac signals, and/or ventricular cardiac signals; and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein. Electrodes are optionally positioned in or via such tributary veins.

Accordingly, an exemplary coronary sinus lead 106 is optionally designed to generate a potential field, sense potentials or signals and/or to deliver pacing therapy. For example, therapy may include left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of generating potential fields, sensing potential and/or cardiac signals, and delivering stimulation in the form of pacing and shock therapy to the right ventricle. An exemplary right ventricular lead may also include at least one electrode capable of stimulating an autonomic nerve and/or anchoring the lead, such an electrode may be positioned on the lead or a bifurcation or leg of the lead.

Figure 2:
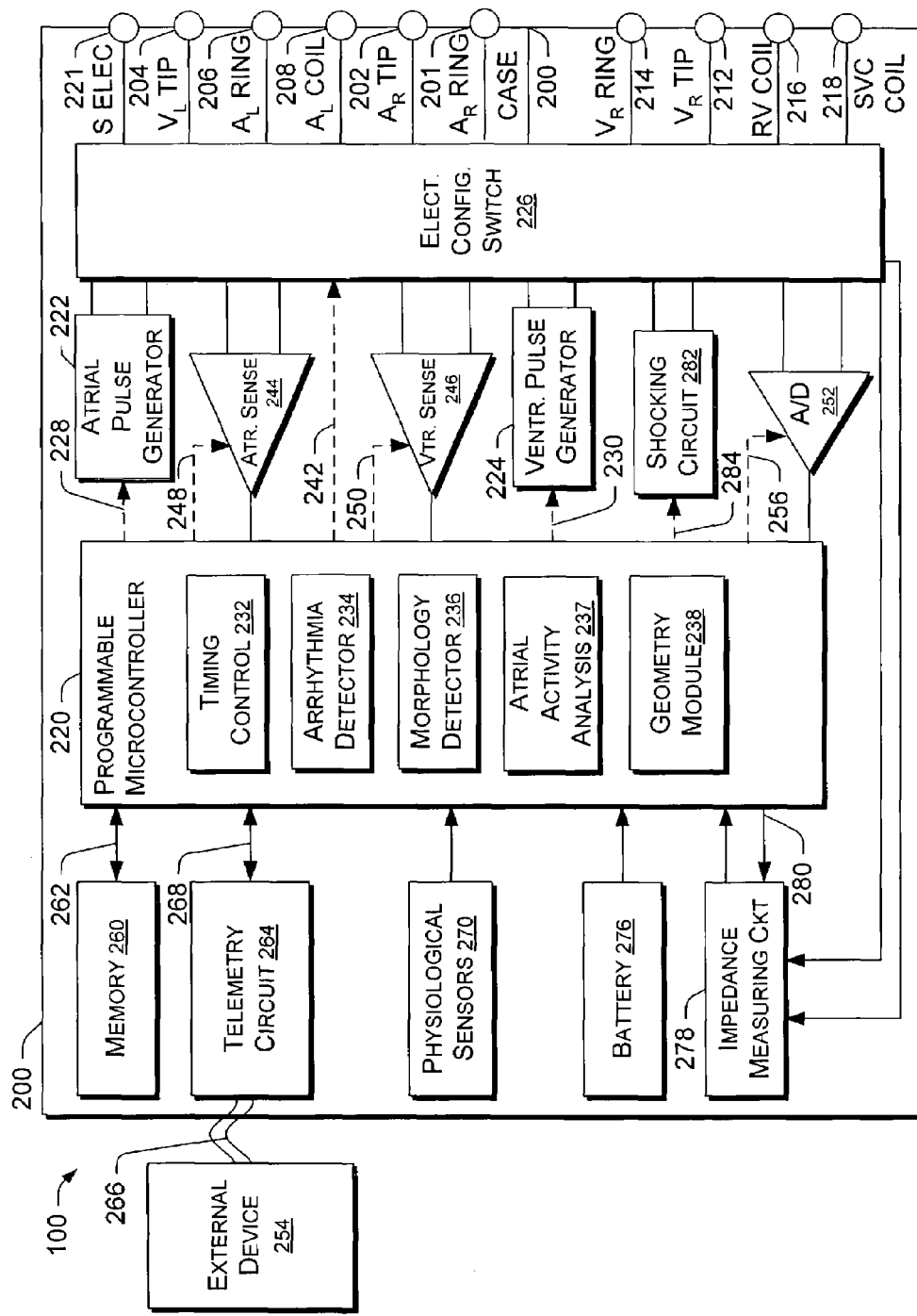
FIG. 2 is a functional block diagram of a multi-chamber implantable stimulation device illustrating basic elements that are configured to generate potential fields, sense potentials and to provide cardioversion, defibrillation, and pacing stimulation to the heart and/or other tissues stimulation in various places in a patient's body.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable implantable device that can generate potential fields and sense potentials. Accordingly, one of skill in the art could readily duplicate, eliminate, or disable the appropriate circuitry in any desired combination to provide a device capable of generating potential fields and sensing potentials and optionally treating appropriate chamber(s) with cardioversion, defibrillation, and/or pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial generating, sensing and/or pacing, the connector includes at least a right atrial tip terminal (AR TIP) 202 adapted for connection to the atrial tip electrode 120. To achieve left chamber generating, sensing, pacing, and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber generating, sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of operation. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art. As described herein, an implantable device includes potential field generating and potential field sensing capabilities, which are optionally controllable via a microcontroller.

Representative types of control circuitry that may be used in connection with various exemplary device and/or methods described herein can include aspects of the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within a typical stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate potential field and/or pacing stimulation pulses for delivery by the right atrial lead 104, the coronary sinus lead 106, and/or the right ventricular lead 108 via an electrode configuration switch 226. It is understood that in order to generate potential fields and/or to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit potential field generation and/or stimulation pulses.

Microcontroller 220 further includes timing control circuitry 232 to control the timing of potential field generation, potential sensing and/or stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to generate potential fields and sense potentials and/or to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 optionally includes a geometry module 238 for performing a variety of tasks related to use of an exemplary methods, as described in more detail below. The geometry component can be utilized by the implantable device 100 for aiding in implantation or positioning, electrode selection (configuration, polarity, etc.), potential field generation, potential sensing, geometry determinations, and/or administration of various therapies, including tissue stimulation to affect the myocardium and/or other tissue and/or nerves. The geometry module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of potential field generations, potential sensing and/or stimulation pulses (e.g., unipolar, bipolar, combipolar, etc.) by selectively closing the appropriate combination of switches (not shown).

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. In addition, such circuits are optionally used to sense potentials, for example, in a potential field. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of any sensed signal by selectively closing the appropriate switches. In this way, the clinician may program the sensing polarity independent of potential field generation and/or stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, to selectively sense the signal (or potential) of interest. The automatic gain control enables the device 100 to deal effectively with the difficult problem of sensing low amplitude signal characteristics associated with atrial or ventricular fibrillation.

The outputs of the atrial and ventricular sensing circuits 244 and 246 are connected to the microcontroller 220, which, in turn, is able to trigger or inhibit the pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. In addition, sensed information is optionally used to time potential field generation and/or potential sensing. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246.

For arrhythmia detection, the device 100 utilizes the atrial and ventricular sensing circuits, 244 and 246, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.)

in order to determine the type of remedial therapy that is needed (e.g., bradycardia pacing, anti-tachycardia pacing, cardioversion shocks or defibrillation shocks, collectively referred to as "tiered therapy").

Cardiac signals and/or sensed potentials are also applied to inputs of an analog-to-digital (A/D) data acquisition system 252. The data acquisition system 252 is configured to acquire intracardiac electrogram (IEGM) signals and/or potentials, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample potentials and/or cardiac signals across any pair of desired electrodes (including can or case or other electrodes).

The microcontroller 220 is further coupled to a memory 260 by a suitable data/address bus 262, wherein the programmable operating parameters used by the microcontroller 220 are stored and modified, as required, in order to customize the operation of the implantable device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and status information relating to the operation of the device 100 (as contained in the microcontroller 220 or memory 260) to be sent to the external device 254 through an established communication link 266.

The implantable device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the implantable device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The implantable device additionally includes a battery 276 that provides operating power to all of the circuits shown in FIG. 2. For the implantable device 100, which may employ shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The implantable device 100 can further include magnet detection circuitry (not shown), coupled to the microcontroller 220, to detect when a magnet is placed over the implantable device 100. A magnet may be used by a clinician to perform various test functions of the implantable device 100 and/or to signal the microcontroller 220 that the external programmer 254 is in place to receive or transmit data to the microcontroller 220 through the telemetry circuits 264.

The implantable device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. Further aspects of impedance are described below.

In the case where the implantable device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Cardiac Geometry Determinations

Figure 3:
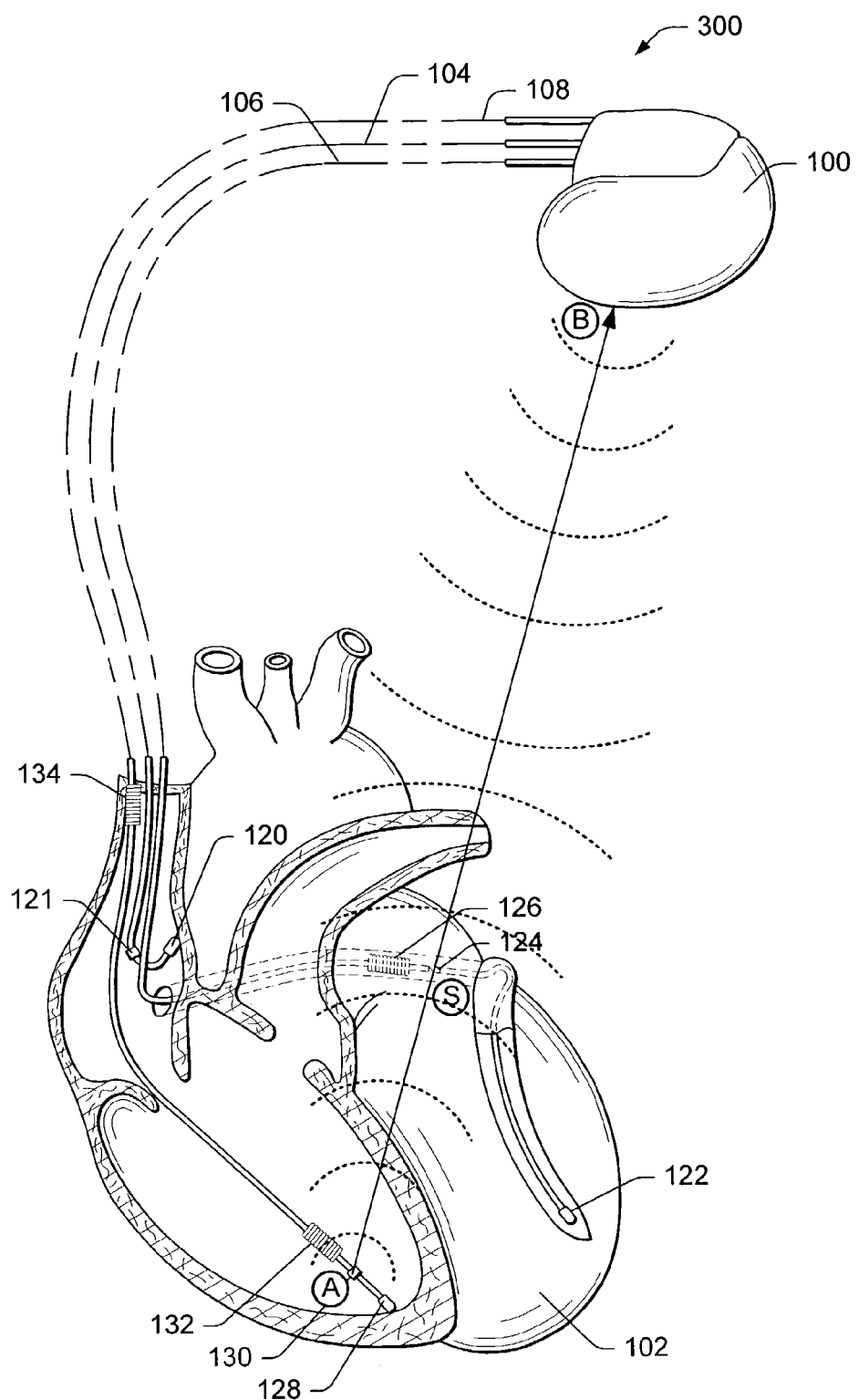
FIG. 3 is a simplified diagram illustrating an implantable stimulation device in electrical communication with leads implanted into a patient's heart for delivering signals and/or sensing.

Various exemplary diagnostics and therapies rely on geometry determinations. FIG. 3 shows an exemplary signal delivery and sensing arrangement 300 having features such as those shown in the implantable device 100 of FIG. 1. The exemplary device 100 has a can or case electrode, which is programmably selected to act as the return electrode for two unipolar configurations. A first unipolar configuration includes the ring electrode 130 of the right ventricular lead 108 and the case electrode of the device 100. A second unipolar configuration includes the ring electrode 124 of the left ventricular lead 106 and the case electrode of the device 100.

According to this exemplary arrangement 300, an electrical signal, delivered by a unipolar delivery circuit generates a potential field between the ring electrode 130 and the case electrode of the device 100. The potential field includes the ring electrode 124, which forms a unipolar sense circuit that includes the case electrode of the device 100. The unipolar sense circuit can sense a potential in the potential field at a point corresponding to the ring electrode 124.

The exemplary arrangement 300 may be supported by the following theory. First consider a single electrode placed in an electrically homogenous medium (e.g., having resistivity ρ) and having a current I measured in amperes. The potential, U, measured in volts, at any point in the medium is given as:

$$U = \rho \frac{I}{2\pi r} \quad (1)$$

where r is the distance from the electrode. For a pair of electrodes (e.g., the can electrode of the device 100 and the ring electrode 130) having current/at electrode A and current –I at electrode B, the potential U is given by the algebraic sum of the individual contributions:

$$U = \rho \frac{I}{2\pi r_A} - \rho \frac{I}{2\pi r_B} = \frac{\rho I}{2\pi}\left[\frac{1}{r_A} - \frac{1}{r_B}\right] \quad (2)$$

where $r_A$ and $r_B$ are the distances from the point (e.g., sense electrode, S) to the electrode A and the electrode B, respectively. Of course, potentials may be sensed at more than one point by more than one electrode or a potential may be sensed in a bipolar manner between two sensing electrode. In the latter case, the potential could be approximated by $U=U_1-U_2$ (3). Equation 3 is an approximation that typically becomes more accurate for an increasingly large medium where nonlinear effects near an electrode or electrodes are minimal.

Figure 4:
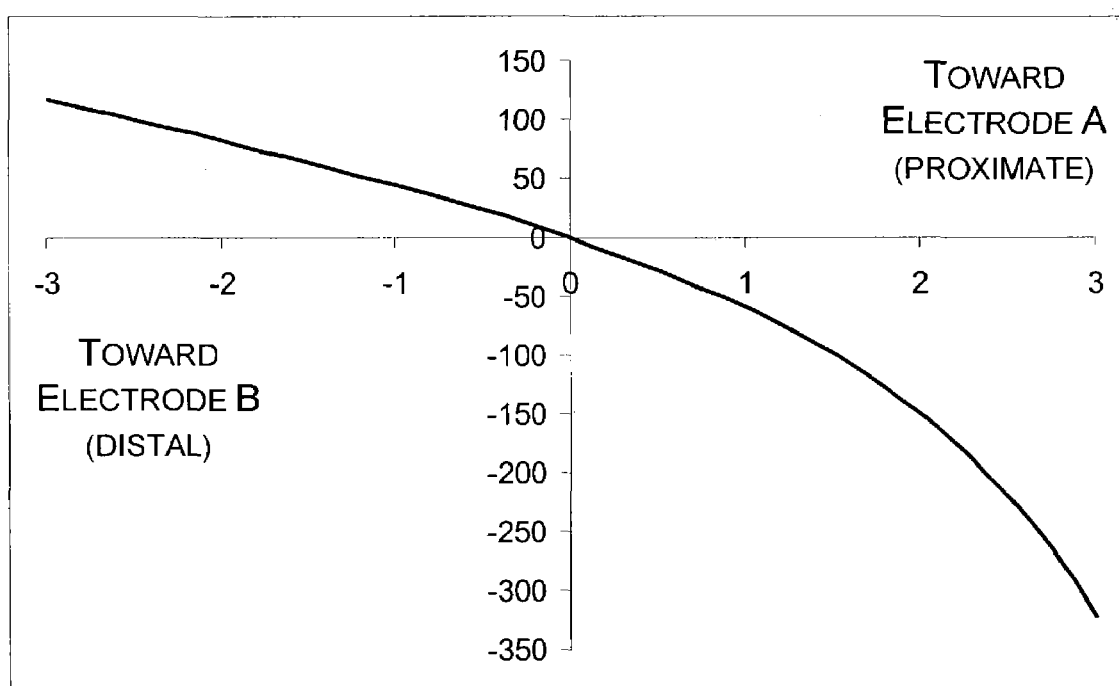
FIG. 4 is an exemplary plot of displacement of a sensor electrode versus percentage change in potential sensed by the sensor electrode.

FIG. 4 shows an exemplary plot 400 of displacement (e.g., of myocardial tissue) versus percentage change in potential using Equation 2. The plot corresponds to a hypothetical scenario wherein the distance between electrodes A and B is approximately 15 cm and the distance between a sense electrode and electrode B (e.g., case or other electrode) is approximately 10 cm and the distance between the sense electrode and electrode A (e.g., ring, tip or other electrode) is approximately 5 cm. According to Equation 2, a displacement of 2.5 cm of the sense electrode along a line toward electrode B results in approximately a 100% change in the potential sensed by the sense electrode (e.g., –0.1° C. to 0° C., where C is a constant) whereas a displacement of 2 cm of the sense electrode along a line toward electrode A results in approximately a 150% change in the potential sensed by the sense electrode (e.g., –0.1° C. to –0.25° C., where C is a constant). Of course, if the displacement occurred along an equipotential line, then no change in potential would be expected. In general, exemplary arrangements avoid positioning of a sense electrode where displacement would occur along an equipotential line.

Note that Equation 2 relies on a resistivity ρ that corresponds to an electrically homogenous medium; a discussion of various exemplary techniques that pertain to non-homogenous media and impedance appears further below. Further note that use of Equation 2 for displacement measurements in relationship to percentage change, etc., in potential does not require knowledge of resistivity ρ, see Equation 4.

$$\%U = 100*(U_1 - U_2)/U_1 = 100*\left[1 - \left[\frac{1}{r_{A2}} - \frac{1}{r_{B2}}\right] * \left[\frac{1}{r_{A1}} - \frac{1}{r_{B1}}\right]^{-1}\right] \quad (4)$$

Ageometry determination (e.g., a position, a displacement, etc.) may rely simply on a sensed potential which is correlated with a geometric parameter. For example, as explained in more detail below, the exemplary arrangement 300 is capable of delivering an electrical signal, sensing a potential, and determining a distance based on the sensed potential. In general, the arrangement 300 is capable of sensing a potential that is related to the physical distance between the case electrode of the device 100 and/or the ring electrode 130 and the ring electrode 124. In addition, the arrangement 300 is capable of sensing a potential that is related to the physical displacement of the ring electrode 124 or one of the other electrodes (e.g., the ring electrode 130).

Figure 5:
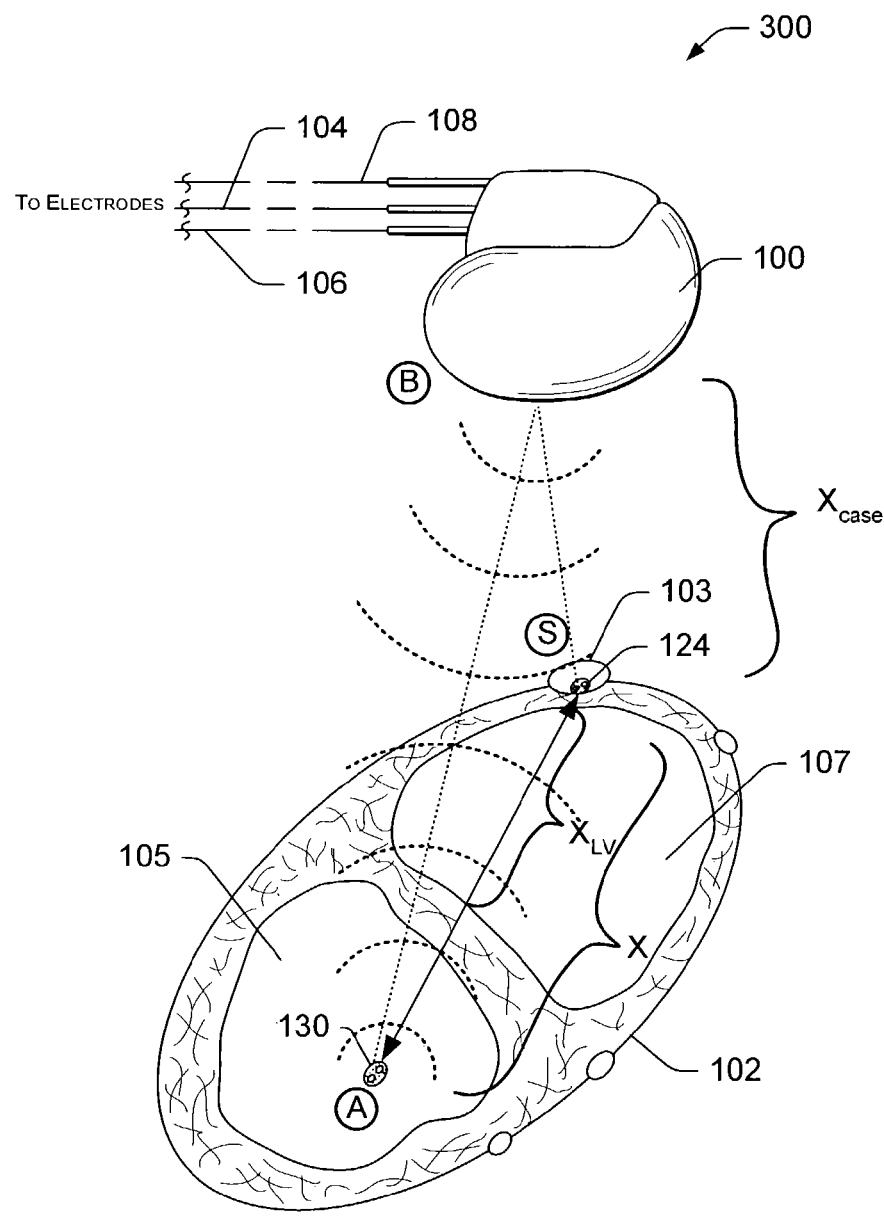
FIG. 5 is a simplified diagram illustrating an implantable stimulation device in electrical communication with leads implanted into a patient's heart for delivering signals and/or sensing wherein the heart is shown in cross-section.

FIG. 5 shows another view of the exemplary arrangement 300. In this cross-sectional view of the heart 102, the right ventricle 105 and the left ventricle 107 are visible. The ring electrode 130 is located in the right ventricle 105 while the ring electrode 124 is located in the coronary sinus 103, posterior to the left ventricle 107. As shown, "x" represents a point-to-point distance between the ring electrode 130 (e.g., electrode A) in the right ventricle 105 and the ring electrode 124 in the left ventricle 107 (e.g., sense electrode S), "$x_{LV}$" represents an approximate distance across the left ventricle 107, and "$x_{case}$" represents an approximate distance between the ring electrode 130 and the case of the device 100 (e.g., electrode B). This particular arrangement 300 is suitable for determining a myocardial tissue displacement and/or displacements with respect to time.

Figure 6:
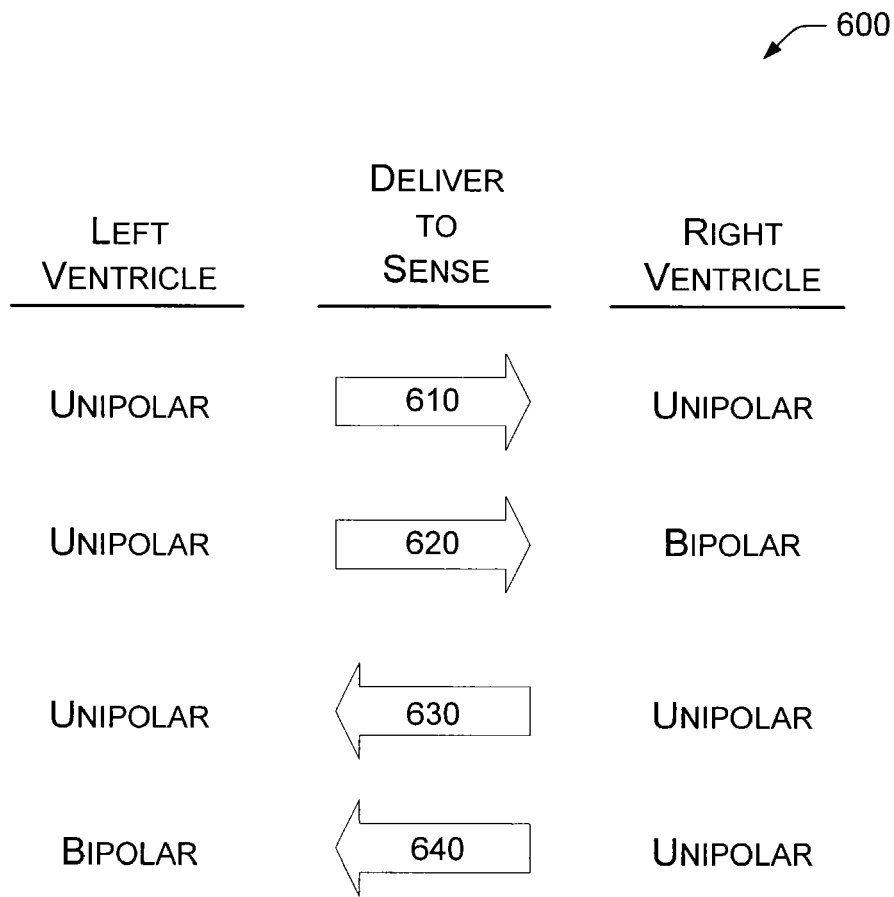
FIG. 6 is a diagram of various exemplary electrode configurations for delivering signals and/or sensing.

While the exemplary arrangement 300 includes a unipolar delivery circuit and a unipolar sense circuit, other configurations are also possible. For example, FIG. 6 shows a variety of possible exemplary delivery and sense configurations 600 (e.g., 610, 620, 630, 640). In these exemplary configurations 600, the delivery circuit generates a potential field and the sense circuit senses a potential in the field. Exemplary configuration 610 includes a left ventricular unipolar delivery circuit and a right ventricular unipolar sense circuit; exemplary configuration 620 includes a left ventricular unipolar delivery circuit and a right ventricular bipolar sense circuit; exemplary configuration 630 includes a right ventricular unipolar delivery circuit and a left ventricular unipolar sense circuit; and exemplary configuration 640 includes a right ventricular unipolar delivery circuit and a left ventricular bipolar sense circuit.

In more specific examples, in the exemplary configuration 610 the test current is delivered between the LV tip and the can while the voltage is sensed between the RV tip (or ring) and the can; in the exemplary configuration 620 the test current is delivered between the LV tip and the can while the voltage is sensed between the RV tip and ring; in the exemplary configuration 630 the test current is delivered between the RV tip and the can while the voltage is sensed between the LV tip (or ring) and the can; and, in the exemplary configuration 640 the test current is delivered between the RV tip and the can while the voltage is sensed between the LV tip and ring.

Figure 7:
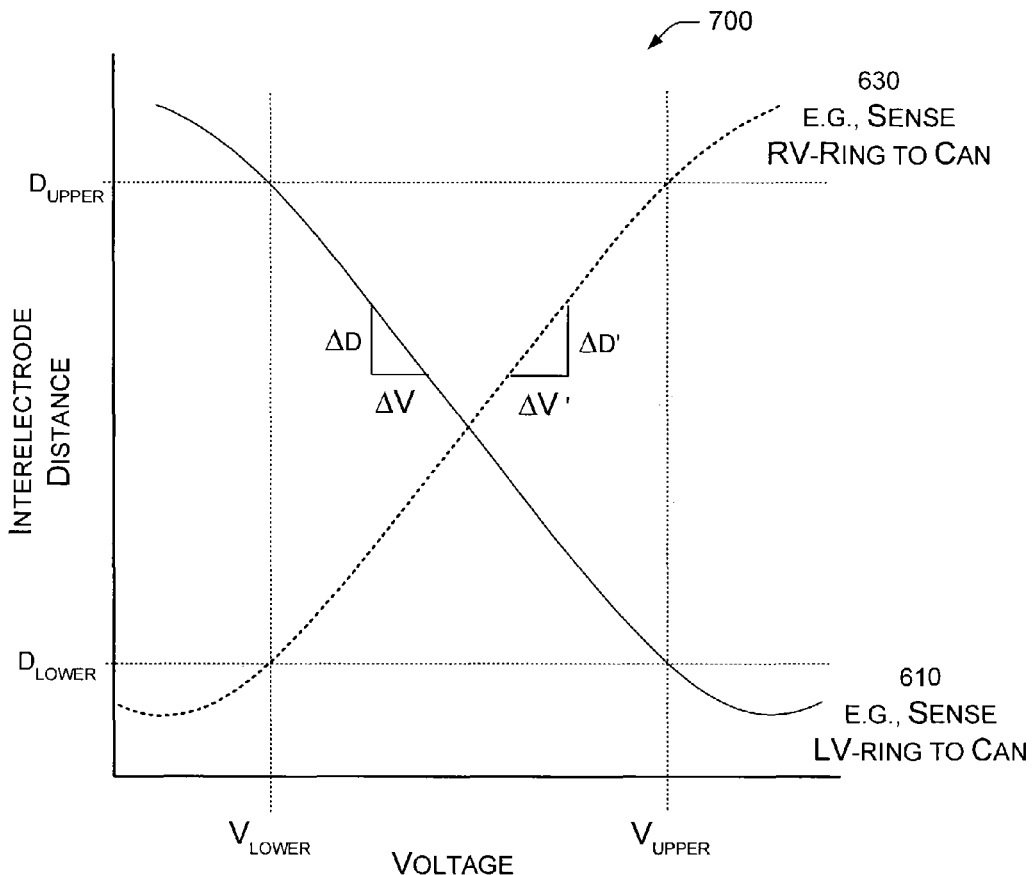
FIG. 7 is a plot of a geometric parameter versus a sensed value wherein a substantially linear relationship exists for at least a portion of the plot.

FIG. 7 shows an exemplary plot 700 of distance versus potential (e.g., voltage). The plot 700 includes a LV-ring to can sense curve 610 and a RV-ring to can sense curve 630. The LV-ring to can sense curve 610 represents potentials sensed in a potential field generated by a RV-ring to can delivery signal while the RV-ring to can sense curve 530 represents potentials sensed in a potential field generated by a LV-ring to can delivery signal. For example, delivery of a signal to the RV-ring (e.g., unipolar) at a potential of 630 mV RMS and a frequency of 1 kHz resulted in a sensed potential of approximately 0 mV to approximately 10 mV, which was substantially proportional to distance between the ring electrodes, which ranged from approximately 0 cm to approximately 15 cm. FIG. 7 indicates two substantially linear portions of the curves wherein the relationship between distance and potential fits a linear model. In the above example, a substantially linear portion for distance versus potential extended between approximately 4 cm and approximately 10 cm. This range corresponds well with dimensions of interest in the human heart. Of course, nonlinear models may extend the fit to a broader range of potentials and distances and/or improve the fit. In addition, conventional leads and electrodes may be used, or adapted for use, to determine geometric parameters for other regions of the body, which may have distance ranges less than and/or greater than those associated with the heart.

Thus, as described herein, exemplary methods and/or devices are suitable for determining geometric parameters of myocardial tissue, including, but not limited to, position and/or displacement.

Figure 8:
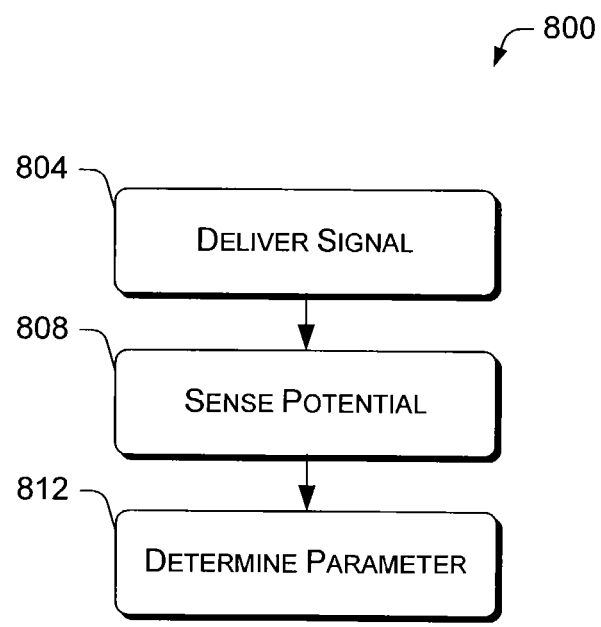
FIG. 8 is a block diagram of an exemplary method for determining a geometric parameter.

FIG. 8 shows an exemplary method 800 for determining a geometric parameter. According to the method 800, a delivery block 804 delivers an electrical signal to generate a potential field. At the same time, or shortly thereafter, a sense block 808 senses a potential in the potential field. A determination block 812 follows that determines a geometric parameter based, at least in part, on the potential.

Figure 9:
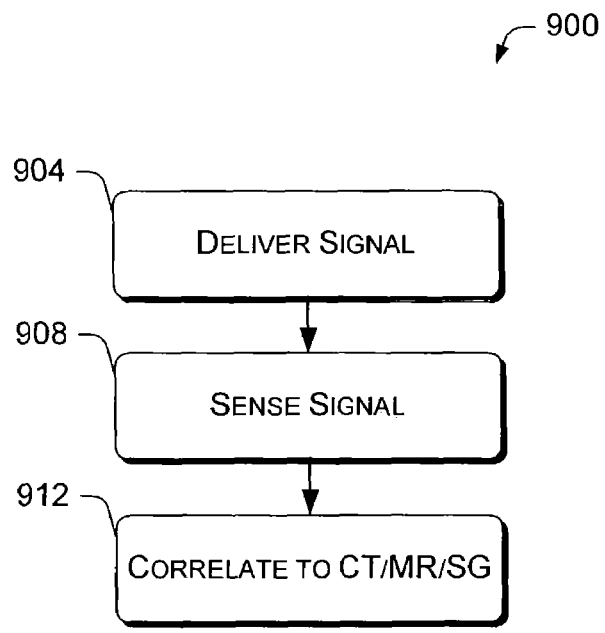
FIG. 9 is a block diagram of an exemplary method for determining a relationship between a sensed value and a geometric parameter.

FIG. 9 shows an exemplary method 900 for correlating sensed potentials with physiologic geometry (e.g., coordinates, distances, displacements, areas, volumes, etc.). According to the method 900, a delivery block 904 delivers an electrical signal to generate a potential field. At the same time, or shortly thereafter, a sense block 908 senses a potential in the potential field. A correlation block 912 follows that correlates one or more sensed potentials to geometric information obtained via a medical imaging device, such as, but not limited to, x-ray, CT, MR, sound-based imaging, etc. The correlation is optionally saved in an implantable cardiac therapy device (e.g., as a model, database, etc.).

Impedance Measurement/Compensation

As mentioned above, Equation 2 relies on a resistivity ρ associated with an electrically homogenous medium. Depending on the circumstances, such an assumption may suffice. For example, changes in an average resistivity with respect to time may have an insignificant effect on sensed potential when compared to changes that occur in sensed potential with respect to displacement Referring to FIG. 4, note that a 2 cm change In displacement of the sense electrode along a line toward electrode A (e.g., an electrode positioned at a distance from a pacing device) resulted in approximately a 150% change in potential. This is due to the relationship between the variables $r_A$ and $r_B$ of Equation 2 and the potential. In contrast, according to Equation 2, the resisitivity ρ would have to change by 150% to have a similar effect on the potential. Thus, in some circumstances, changes in resistivity ρ may have little effect on the sensed potential compared to displacement In addition, for a potential measurement that includes a device case as part of a sensing circuit, the effect of changes in a chamber's blood volume may have an insignificant effect on an average resistivity ρ because the composition of the media in the potential field remains relatively constant (i.e., averaged over a volume that Is much larger than chamber volume).

For circumstances that warrant knowledge of impedance for compensation or correction of distance or displacement or for determining other useful information, an exemplary device and/or an exemplary method may rely on direct and/or indirect impedance measurement. In general, resistivity ρ of a heterogenous medium will depend on resistivifies of component media and amount of and/or orientation of component media. Regarding cardiac impedance (e.g., between opposing walls of a chamber), an average resistivity may depend on myocardial resistivity, blood resistivity, blood area/volume and orientation, and myocardial area/volume and orientation. Blood area/volume certainly varies with respect to time and, where warranted, impedance techniques that can estimate blood area/volume may be used to complement distance and/or displacement measurements.

Impedance is typically defined as total passive opposition offered to the flow of electric current. Biological impedance may have a relatively constant component and a time variant component. For example, cardiac output (CO) has been related to a constant impedance component, $Z_0$, and a time variant impedance component, $Z(t)$, the latter of which may be given as:

$$Z(t) = T\frac{dZ}{dt} \qquad (5)$$

where Z is impedance in ohm and T is a systolic or left ventricular ejection time in seconds. Sometimes Z(t) is given as the sum of $Z_o$ plus a time varying component.

Stroke volume (SV, in ml) may be estimated as follows:

$$SV = \rho_B \times (L^2/Z_0^2) * T \frac{dZ}{dt} \qquad (6)$$

where $\rho_B$ is the resistivity of the blood in ohm*cm and L is the distance in cm between two electrodes. Cardiac output (CO) may then be calculated as stroke volume (SV) multiplied by heart rate (HR).

Another impedance technique known as impedance plethysmography can estimate a chamber volume. According to this technique, impedance of blood is related to a chamber volume. To perform this technique, a lead having at least two electrodes is inserted into a chamber of the heart. Electrical resistance of a conductor is given as:

$$R = \frac{\rho L}{A} \qquad (7)$$

where R is resistance in ohms, $\rho$ s resisitivity of the conductor in ohm*cm, L is the distance between two electrodes in cm and A is the cross-sectional area of the conductor in cm². A current I is applied to the two electrodes and a potential U is measured in volts between the two electrodes. A resistance R is calculated by dividing potential U by current I. Resistivity $\rho$ of blood is known a priori, which allows a determination of A, the cross-sectional area of the conductive blood. A series of electrodes on a lead may be used to determine a series of cross-sectional areas $A_i$ for a series of distances $L_i$. Individual volumes $V_i$ (e.g., i=1 to n) may be determined by multiplying $A_i$ and $L_i$ and a total volume $V_T$ by summing the individual volumes $V_i$.

In general, contraction of a ventricle results in a decrease in ventricular cross-sectional area (e.g., A); thus, per Equation 7, where blood is the main conductor, a ventricular contraction corresponds to an increase in resistance, which results in an increase in potential for a given current I, assuming L, the distance between two measuring electrodes remains constant.

Figure 10:
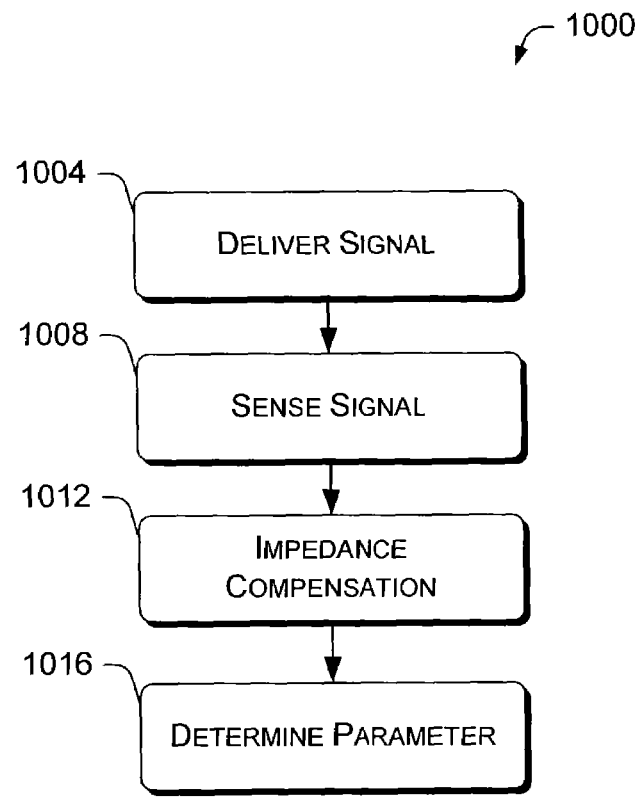
FIG. 10 is a block diagram of an exemplary method for compensating for impedance and determining a geometric parameter.

FIG. 10 shows an exemplary method 1000 for compensating for changes in impedance. According to the method 1000, a delivery block 1004 delivers an electrical signal to generate a potential field. At the same time, or shortly thereafter, a sense block 1008 senses a potential in the potential field. An impedance compensation block 1012 follows that compensates for changes in impedance, for example, changes that may effect a preexisting correlation between potential and geometry. A determination block 1016 follows the compensation block 1012 that determines a geometric parameter based, at least in part, on the potential and the impedance compensation.

The exemplary method 1000 may compensate for deviations in a potential field due to variability in tissue and body fluid. An exemplary arrangement, useful for unipolar signal delivery, includes delivering via a larger electrode (e.g., usually a ring or coil electrode) and sensing via a local voltage at the associated tip to determine impedance.

Another method for detecting or adjusting for an increased resistance or an impedance variation is simply to look at the classic impedance given from measured pacing data. For example, if a great deal of fibrosis exists near an electrode (e.g., RV-ring), it may lead to a resistance increase that should show in the measured data of pacing resistance, which uses the electrode in a bipolar configuration. Measurement of resistance for unipolar RV-ring pacing may also be available.

Real-time Ventricular Function

Various aforementioned exemplary potential sensing methods can allow for real-time or near real-time ventricular function monitoring. Further, such exemplary methods are optionally used in conjunction with traditional methods (e.g., impedance plethysmography) to enhance diagnostics and/or therapy. With respect to left ventricular monitoring, a left ventricle, which is myocardial tissue, can assume a larger, more spherical (globular) shape after injury such as myocardial infarction. Noninfarcted failing myocardium undergoes similar time-dependent changes that have been attributed to side-to-side slippage, increased myocyte length, and left ventricular hypertrophy. The result is a shift in left ventricular geometry from a prolate ellipse to a more spherical shape. This in turn causes increased meridianal wall stress, abnormal distribution of fiber shortening, functional mitral regurgitation, worsened exercise tolerance, and poorer long-term survival. As described herein, various exemplary methods may monitor, diagnose and/or compensate for changes in ventricular geometry with respect to time.

An exemplary method monitors geometric and/or mechanical parameters to monitor a CHF patient's left ventricular function for significant signs of progressive heart failure in terms of mechanical failure as it is expressed by one or more changing heart pump parameters, which in turn may alert a physician to more aggressively treat the CHF patient in an effort to delay or possibly halt progression of the disease.

Figure 11:
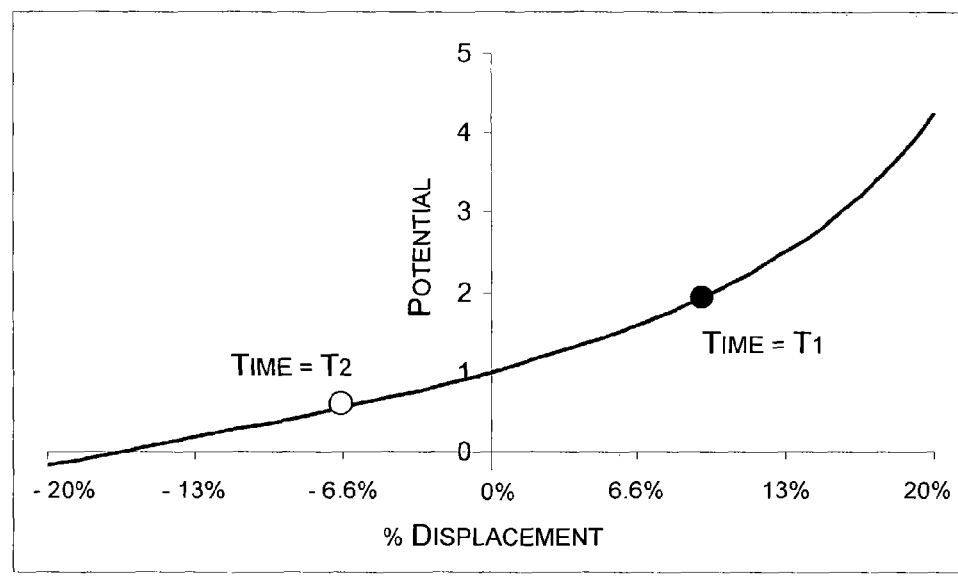
FIG. 11 is an exemplary plot of normalized potential versus percent displacement of a sense electrode with reference to two potential field electrodes and a corresponding exemplary plot of normalized potential and percent displacement versus time.
Figure 11:
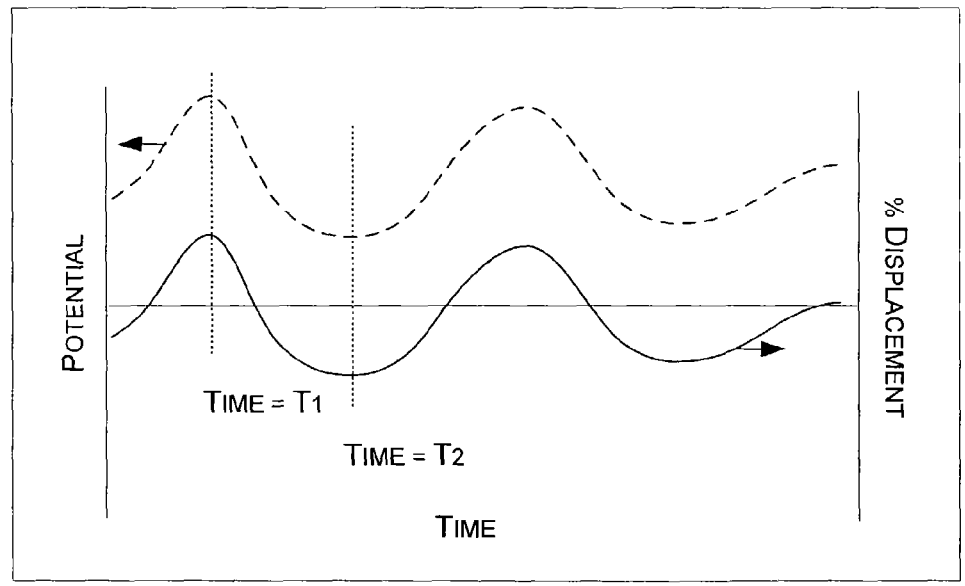

FIG. 11 shows a plot 1110 of normalized potential versus percent displacement and a plot 1120 of normalized potential with respect to time. The plots 1110, 1120 show normalized potentials measured at a sense electrode which is displaced with respect to two other electrodes (e.g., electrodes A and B) that generate a potential field. The percent displacement is a positive or negative displacement of the sense electrode (e.g., $\Delta X_{sense}$) given as a percentage of the distance between the potential field generating electrodes (e.g., $100 * \Delta X_{sense}/\Delta X_{field}$). The plot 1110 may be used to correlate an instantaneous potential measured by the sense electrode with a displacement percentage or value. Of course, a plot of potential versus position could also be used to determine a position based on a measured potential. The plot 1120 includes instantaneous potential and percent displacement with respect to time wherein the percent displacement is based on a correlation of potential with respect to percent displacement per the plot 1110. For example, time T1 corresponds to a positive displacement of the sense electrode while time T2 corresponds to a negative displacement of the sense electrode. As described below, such time varying displacements may be characteristic of a sense electrode placed in or on a chamber of the heart.

An exemplary method for measuring real-time ventricular function includes positioning one electrode at the apex of the right ventricle and positioning another electrode in the coronary sinus adjacent to the left ventricle. In this example, the two electrodes have associated leads that connect to an implantable device, which may have a case that acts as a third electrode. A potential field is generated using the electrode positioned at the apex of the right ventricle and the case of the implantable device while a potential is sensed using the electrode positioned in the coronary sinus. The sensed potential is then used to determine a geometric parameter of the heart.

With respect to human anatomy, a study by Dong, et al., "Regional left ventricular systolic function in relation to the cavity geometry in patients with chronic right ventricular pressure overload: A three-dimensional tagged magnetic resonance imaging study, Circulation, 91(9):2359–2370 (1995), showed a relationship between the longitudinal systolic descent of markers and their corresponding end-diastolic distance from the epicardial apex for patients with healthy hearts and diseased hearts. In the healthy hearts, the markers were set at end-diastolic distances of approximately 2.5 cm, 4.2 cm, 5.8 cm and 7.2 cm from the epicardial apex, which moved little compared to longitudinal systolic descent of the markers, and the corresponding longitudinal systolic descents of the markers were approximately 0.3 cm, 0.6 cm, 0.9 cm and 1.1 cm, respectively. The diseased hearts, patients diagnosed with chronic right ventricular pressure overload, exhibited significantly smaller descents (e.g., approximately 0.2 cm, 0.3 cm, 0.5 cm, and 0.7 cm based on linear interpolation).

Thus, for the aforementioned exemplary method, the following assumptions are possible: (i) an end diastolic distance of approximately 7.2 cm between the epicardial apex and the sense electrode; (ii) an end diastolic distance of approximately 5 cm between the right apex electrode and the coronary sinus sense electrode; and (iii) a relatively constant distance of approximately 15 cm between the right apex electrode and the case electrode. Given these assumptions and the data of Dong, et al., an approximate 1 cm longitudinal systolic descent of the coronary sinus sense electrode will result in about a 50% change in sensed potential, compared to the end diastolic sensed potential.

In instances where timing of the sensed potential is a concern, left ventricular diastolic volume typically reaches a maximum shortly after atrial contraction and left ventricular systolic volume typically reaches a minimum shortly after or during repolarization. Thus, potential field generation and/or sensing may occur based on P wave and/or T wave timings. For example, a diastolic sensed potential may occur after detection of a P wave or delivery of an atrial stimulus and a systolic sensed potential may occur after detection of a T wave, an R wave plus a delay or delivery of a ventricular stimulus plus a delay.

Figure 12:
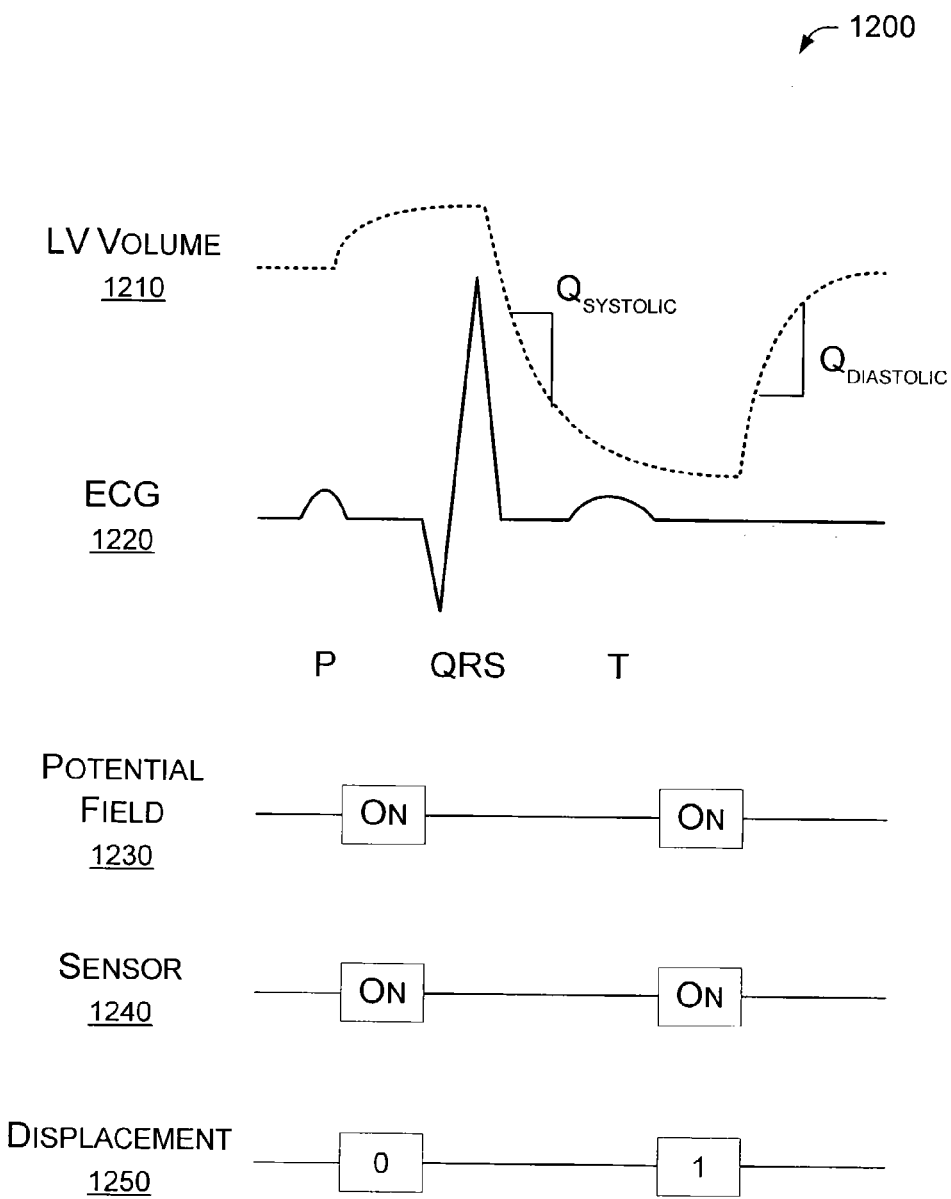
FIG. 12 is an exemplary scheme that includes a plot of left ventricular volume versus time, an ECG plot, a potential field timing channel, a sensor timing channel and displacements corresponding to sensed displacements.

FIG. 12 shows an exemplary method 1200 for sensing displacement associated with a left ventricle. A plot of left ventricular (LV) volume versus time 1210 is shown in conjunction with an electrocardiogram (ECG) 1220, which includes labels for a P wave, a QRS complex and a T wave. The plot 1210 also includes labels for a systolic volumetric flow rate $Q_{systolic}$ and a diastolic volumetric flow rate $Q_{diastolic}$, which are based on the slope of the volume-time curve during systole and diastole. According to this exemplary method a potential field channel 1230 generates a potential field between two or more electrodes during a post-P wave generation interval and during a post-T wave generation interval. A sensor channel 1240 senses a potential in the generated potential field during a post-P wave sense interval and during a post-T wave sense interval. The sensed potentials are then correlated with a displacement to yield a post-P wave displacement and a post-T wave displacement. The difference between these two displacements corresponds to changes in left ventricular volume that occur between approximately end diastole and approximately end systole and consequently, the change in displacements may correspond to stroke volume as well. Of course, a variety of other timings are possible for potential field generation and sensing. For example, a constant potential field may be used with periodic sensing or constant sensing may be used with periodic potential field generation.

Figure 13:
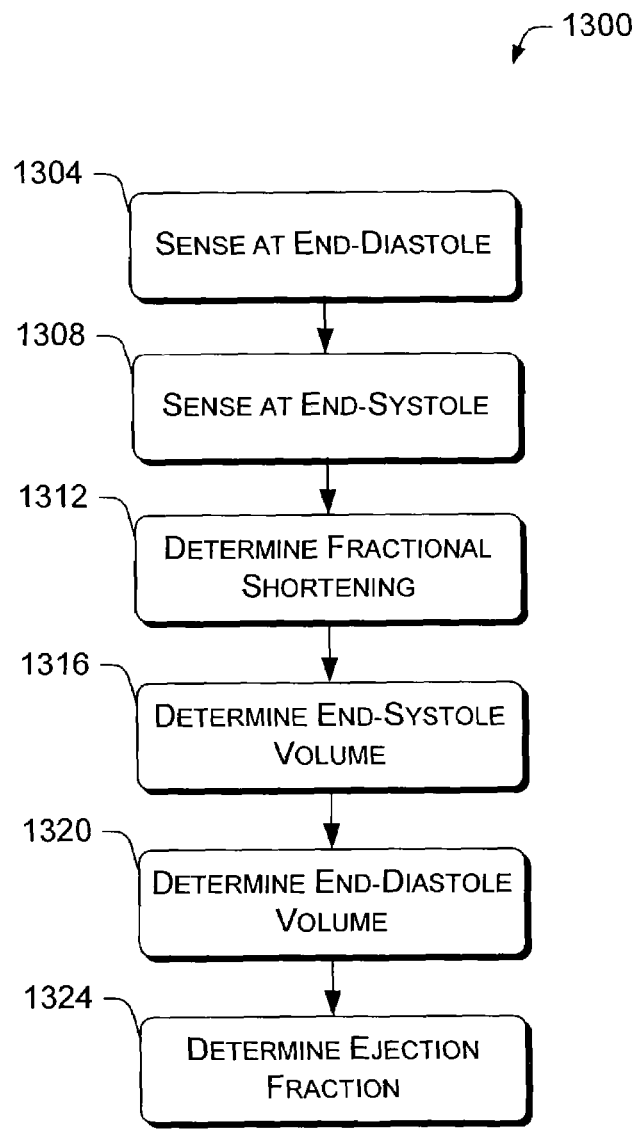
FIG. 13 is a block diagram of an exemplary method for determining fractional shortening and ejection fraction.

FIG. 13 shows an exemplary method 1300 for determining fractional shortening, end-systole ventricular volume, end-diastole ventricular volume and/or ejection fraction. A sense block 1304 uses one or more sense electrodes to sense a potential in a potential field near or at the end of diastole. Another sense block 1308 uses one or more sense electrodes to sense a potential in a potential field near or at the end of systole. According to this method, the potentials sensed in blocks 1304, 1308 correspond to distances and/or displacements. A determination block 1312 uses the sensed potentials directly or indirectly to determine fractional shortening, which may be defined as 1 less the end-systolic length divided by the end-diastolic length (e.g., FS=1−ESL/EDL).

In general, fractional shortening is an accurate evaluation of change in heart geometry. A study by Wandt, "Mitral Ring Motion in Assessment of Left Ventricular Function", *Linköping University Medical Dissertations*, No. 555 (1998) (ISBN 91-7219-069-8; ISSN 0345-0082), shows age related changes in ventricular long and short axes contractions (e.g., major and minor axes). For example, in 40 healthy subjects aged 18–70 years, long axis systolic shortening decreases by 20% and minor axis shortening increases by 18% in a progression from early adult to late adult. Thus, fractional shortening changes over time due to this aging effect. The exemplary method 1300 may compensate for such changes if warranted. In addition, the method 1300 may compare fractional shortening to pre-existing values, such as those published in GEIGY Scientific Tables, Volume 5, Heart and Circulation, edited by Lentner (CIBA-GEIGY, West Caldwell, N.J., 1990). Other data from these tables may be used for determinations, comparisons and/or compensations.

The exemplary method 1300 also includes two determination blocks 1316, 1320 for determination of ventricular volume at end-systole and at end-diastole. The end-diastolic and end-systolic volumes have been shown to have a linear relationship that is useful in the diagnosis of ventricular problems. These volume determinations may rely on various models, such as, but not limited to an ellipsoid model, also referred to as the area-length model or single plane model:

$$V = \frac{\pi}{6} D^2 L \tag{8}$$

where D is the minor axis and L is the major axis. An alternative model is the modified ellipsoidal model, also called the Teichholz model:

$$V = \frac{7}{(2.4 + D)} D^3 \tag{9}$$

where D is now defined as an internal dimension, as determined by echocardiography or in the exemplary method 1300, optionally by sensing a potential in a potential field. Other alternative models include the hemi-cylinder hemi-ellipsoidal model, the disc summation model (e.g., Simpson's rule), and the modified disc summation model.

Once the determination blocks 1316, 1320 determine end-systole volume (EDS) and end-diastole volume (EDV), then another determination block 1324 determines ejection fraction. Ejection fraction (EF) may be determined using the following equation: EF=(EDV−ESV)/EDV (9). Further, the exemplary method 1300 may determine stroke volume (e.g., SV=EDV−ESV), cardiac output (e.g., CO=SV*HR), cardiac index (e.g., CI=CO/body surface area, where body surface area is approximately $71.84*(M^{0.425})*(H^{0.725})$) and/or other parameters. These parameters may assist in treatment and/or diagnosis of cardiac conditions.

An exemplary method combines left ventricular ejection fraction (LVEF) with data derived from an activity test, such as, but not limited to a walk test. For example, consider a six-minute walk test (6'WT) that is used to monitor progressive risk of patient survivability. The 6'WT can determine maximal exercise capacity and provide a prognostic similar to peak $VO_2$. More specifically, a 6'WT is defined by a patient, who sets the pace, walking as far as possible within 6 minutes, using walking with rest and stops as needed. The total distance walked during the six minutes is an output value of the test. In one particular patient population, the mean distance walked during the 6'WT was 455±107 m (range: 170–692 m). Accordingly the exemplary method may combine an LVEF ejection fraction parameter and an outcome of the 6'WT using a two-variable model for heart failure survival. When provided with data over time, the two-variable model can provide a relatively accurate and continuous measure of a patient's prognosis and change thereof depending upon the changes in the patient's LVEF or the patient's 6'WT performance. According to this exemplary method, a physician can continuously and closely monitor an ambulatory patient with advanced heart failure.

A suitable implantable device includes capabilities for evaluating a 6'WT, and for determining ejection fraction. Such a device is suitable for patients that are prescribed a prophylactic implantable device (e.g., ICD). For example, recent results from the MADIT II trial indicate that post-MI patients with an ejection fraction less than approximately 30% (i.e., MADIT II patients) may be eligible for a prophylactic ICD. A multivariable model that includes a LVEF and a 6'WT output variables (e.g., distance walked), can estimate risk of death within a given time period (e.g., 1 year) due to advanced heart failure. For example, the following multivariable model may be implemented to determine risk of death within 1 year:

$$Risk=(-0.0960*LVEF(\%))+(-0.0047*6'WT(m))\ (10)$$

The coefficients, adjusted hazard ratio (95% CI), Wald chi-square, and p values for the multivariable model are given in a study by Zugek, et al., Risk stratification in middle-aged patients with congestive heart failure: prospective comparison of the Heart Failure Survival Score (HFSS) and a simplified two-variable model", *European Journal of Heart Failure*, 3:577–585 (2001), which is incorporated herein by reference. The study found the two-variable model superior to the Heart Failure Survival Score (HFSS). Therefore, such a risk model, when implemented in an implantable device, can improve risk stratification in ambulatory patients with advanced heart failure.

As a left ventricular function monitor, an exemplary implantable device is programmable, and can be preprogrammed to follow and trend one or more mechanical parameters (e.g., cardiac output, cardiac index, stroke volume, stroke volume index, and ejection fraction). In addition, such a device may telemeter parameters to a physician station or a programmer to assist in an ongoing patient monitoring process.

Referring again to the exemplary potential and displacement versus time plot 1120, additional diagnostic and/or therapeutic information may be discerned by considering derivatives with respect to time. A study by Silva, et al., "Study of myocardial contraction and relaxation velocities through Doppler tissue imaging echocardiography: A new alternative in the assessment of the segmental ventricular function", *Arg. Bras. Cardiol.*, 78(2): 206–211 (2002), examined heart movements in 35 healthy individuals. The study determined mean peak systolic and diastolic velocities for basal, medial and apical left ventricular segments. The results indicated that maximum movement velocity is greater during relaxation than during contraction and that the maximum velocity decreased from the base to the ventricular apex, which supports the findings of Dong, et al., that the position of the apex remains relatively constant. Maximum systolic velocities were 7.35 cm/s, 5.26 cm/s, and 3.33 cm/s for basal, medial and apical segments, respectively, while maximum diastolic velocities were 10.56 cm/s, 7.92 cm/s, and 3.98 cm/s for basal, medial and apical segments, respectively. Silva, et al., further noted that the left ventricular velocity vectors are directed generally to a site within the ventricular cavity positioned about 70% of the distance between the base and the apex (i.e., closer to the apex than the base). In addition, Silva, et al., noted that peak systolic velocity occurred at approximately 130 ms after a QRS complex ECG amplitude peak and that peak diastolic velocity occurred at approximately 460 ms after the ORS complex ECG amplitude peak. These peak velocities correspond generally to regions of peak volumetric flow rate shown in the plot 1210 of FIG. 12.

Figure 14:
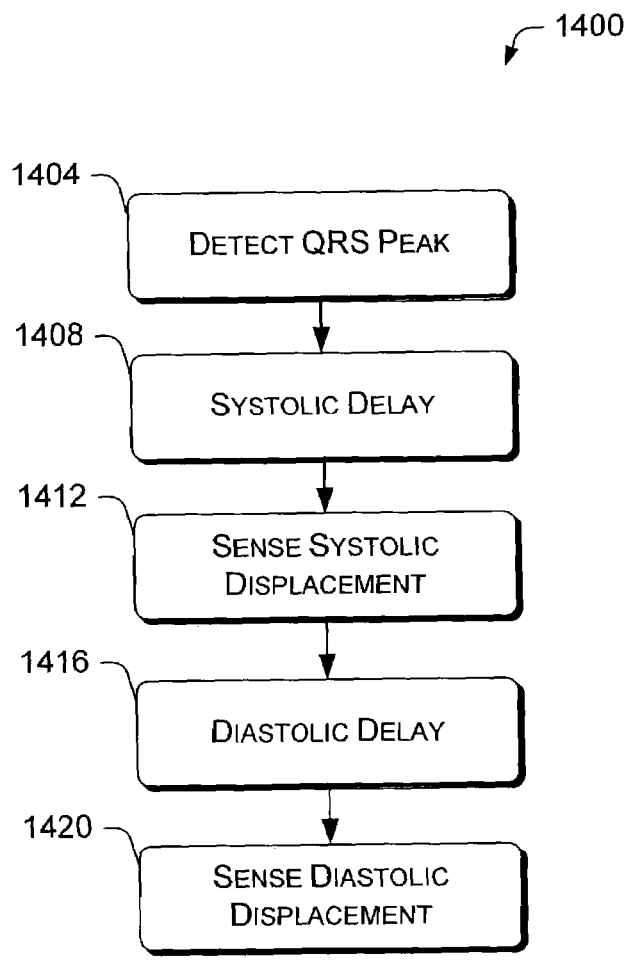
FIG. 14 is a block diagram of an exemplary method for sensing potentials during specific systolic and diastolic intervals.

FIG. 14 shows an exemplary method 1400 for determining maximum left ventricular velocities. In a detection block 1404, a QRS complex or R wave peak is detected. In a delay block 1408, the QRS complex or R wave detection then commences a systolic delay. The systolic delay corresponds to an approximate QRS complex or R wave peak to maximum systolic ventricular velocity interval. After the delay, in a sense block 1412, a sense electrode senses potential in a potential field with respect to time wherein sensed potential corresponds to displacement of a ventricle with respect to time and hence ventricular velocity. A diastolic delay block 1416 follows which commences a diastolic delay that corresponds to an approximate QRS complex or R wave peak to a maximum diastolic ventricular velocity interval minus the systolic delay. Upon expiration of the diastolic delay, in another sense block 1420 a sense electrode senses potential in a potential field with respect to time wherein sensed potential corresponds to displacement of a ventricle with respect to time and hence ventricular velocity. In this example, a systolic delay is set to approximately 100 ms or more and a diastolic delay is set to approximately 300 ms or more. Sensing in the sense blocks 1412, 1420 may also occur for a set period of time, for example, approximately 30 ms to approximately 100 ms.

An exemplary method optionally relies on an implantable and programmable device to determine cardiac information. According to this exemplary method the device delivers a sub-threshold stimulus (e.g., an electrical signal, etc.) using a unipolar configuration (e.g., a case/can electrode and a right ventricular electrode). During the delivery, a bipolar electrode configuration (e.g., a pair of electrodes on a left ventricular lead) is used to sense a potential of the stimulus. In this example, the device then determines a distance between a right ventricular position to a left ventricular position.

In another example, an implantable and programmable device delivers a sub-threshold stimulus using a unipolar electrode configuration (e.g., a case/can and a left ventricular electrode which may be positionable in or proximate to a left ventricle). During this delivery, a bipolar electrode configuration (e.g., a pair of electrodes on a right ventricular lead) is used to sense a potential of the stimulus. In this example, the device then determines a distance between a right ventricular position to a left ventricular position.

Another exemplary method determines instantaneous or near-instantaneous left ventricle diameter. For example, such a determination may rely on a predetermined inverse N relationship, where N=1, 2, 3, or another predetermined exponent: $k*R^N=k_0*(R_0^N)$, where k and $k_0$ are coupling and/or attenuation factors, and $R=R_0*[k_0/k]^{1/N}$, where $R_0$ equals an initial calibrated distance. At the time of implantation of an implantable and programmable device, the term $k_0$ may be determined based on averaged signal strengths of aforementioned right ventricular to left ventricular and left ventricular to right ventricular potential measurements (e.g., see aforementioned exemplary methods for determining distance, etc.). Further, at or near implantation, the factor Ro may be determined using an imaging modality such as Doppler echocardiography. This particular exemplary method may AC-couple detected analog signal data, digitize the signal, compute a signal mean, and then subtract the mean from signal data. Taking the absolute value of the digital signal may occur next followed by determining maximum signal value. For example a maximum signal value may equal a new estimate of signal strength and hence allow for determination of a new k value. Further, a new estimated left ventricular diameter may be determined using the inverse N relationship to get a new estimate of R.

Another exemplary method includes time series analysis of left ventricular diameter. For example, a determined LV diameter measurement subsystem may average distance estimates to compute a left ventricular diameter for Jth time: LV diameter (J)=[(DIST(RV, LV)+DIST(LV, RV))/2]. An implantable and programmable device may adjust ongoing LV diameter measurements using a sliding window technique, with M sliding measurements (where M=2, 4, 8, for example), such that LV diameter (•)=(LV diameter(•)+(LV diameter(J)−LV diameter(J−M+1)))/M. An exemplary implantable and programmable device may alternatively, or in addition to, adjust time series of LV diameters with other trending methods such as MA(p) or AR(q) filter methods.

Pacing Therapy

Figure 15:
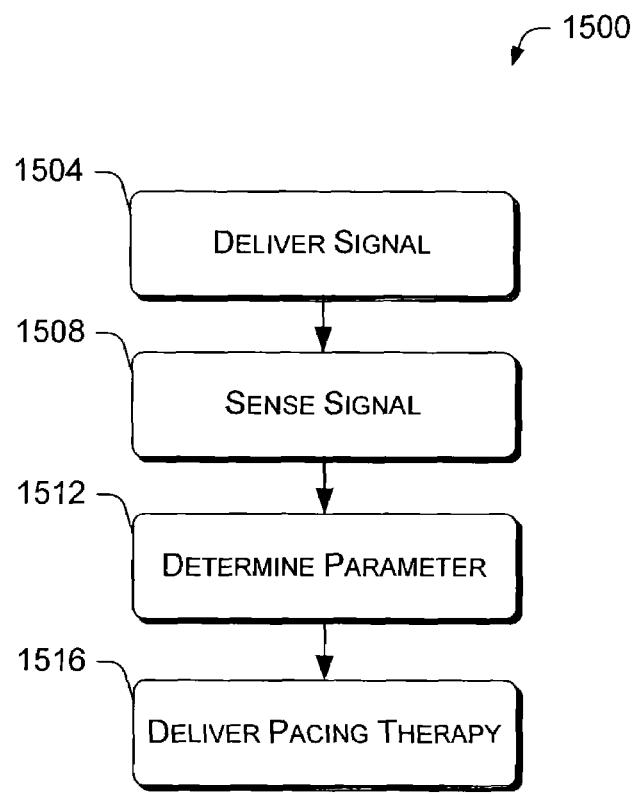
FIG. 15 is a block diagram of an exemplary method for determining a geometric parameter and delivering pacing therapy.

FIG. 15 shows an exemplary method 1500 for determining a geometric parameter. According to the method 1500, a delivery block 1504 delivers an electrical signal to generate a potential field. At the same time, or shortly thereafter, a sense block 1508 senses a potential in the potential field. A determination block 1512 follows that determines a geometric parameter based, at least in part, on the potential.

Various aforementioned exemplary methods, devices and/or systems are optionally used in combination to determine coordinates, for example, in a body defined coordinate system and/or an externally defined coordinate system.

CONCLUSION

Although various exemplary devices and/or methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method comprising:
    determining, in vivo, a myocardial tissue displacement based at least in part on a sensed potential; and
    diagnosing a cardiac condition based at least in part on the displacement.

2. The method of claim 1 wherein determining comprises determining a time derivative of a myocardial tissue displacement based at least in part on a sensed potential.

3. The method of claim 2, wherein the derivative represents one, of myocardial tissue velocity and acceleration.

4. The method of claim 1, wherein determining the myocardial tissue displacement is performed during systole.

5. The method of claim 1, wherein determining the myocardial tissue displacement is performed during diastole.

6. A method comprising:
    determining, in vivo, a myocardial tissue displacement based at least in part on a sensed potential; and
    determining a cardiac therapy based at least in part on the displacement.

7. The method of claim 6 wherein determining comprises determining a time derivative of a myocardial tissue displacement based at least in part on a sensed potential.

8. The method of claim 7, wherein the derivative represents one of myocardial tissue velocity and acceleration.

9. The method of claim 6, wherein determining the myocardial tissue displacement is performed during systole.

10. The method of claim 6, wherein determining the myocardial tissue displacement is performed during diastole.

11. A method comprising:
    determining, in vivo, a left ventricular ejection fraction based at least in part on a sensed potential;
    determining, in vivo, an activity test parameter; and
    determining a survival risk based on the left ventricular ejection fraction and the activity test parameter.

12. A method comprising:
    determining, in vivo, a first myocardial tissue displacement during systole based on a sensed potential;
    determining, in vivo, a second myocardial tissue displacement during diastole; and
    determining the difference between the first displacement and the second displacement.

13. The method of claim 12, wherein the determining a first displacement includes detecting a feature of cardiac activity, initiating a systolic delay, sensing a potential in a potential field, and correlating the potential to a first displacement.

14. The method of claim 12, wherein the determining a second displacement includes detecting a feature of cardiac activity, initiating a diastolic delay, sensing a potential in a potential field, and correlating the potential to a second displacement.

15. The method of claim 12, further comprising determining a cardiac therapy based at least in part on the difference.

16. The method of claim 12, further comprising diagnosing a cardiac condition based at least in part on the difference.

17. The method of claim 12, further comprising determining a fractional shortening based at least in part on the difference.

18. An implantable device comprising:
    means for determining a myocardial tissue displacement based at least in part on a sensed potential; and means for diagnosing a cardiac condition based on the displacement.

19. The implantable device of claim 18 and further comprising:
means for determining a cardiac therapy based on the displacement.

20. An implantable cardiac system comprising:
an implantable device having a case capable of acting as an electrode;
one or more implantable leads having one or more electrodes wherein the one or more leads are connectable to the device; and
circuitry that is operative to deliver an electrical signal to a first electrode position in or adjacent to a cardiac chamber, sense a potential generated by the delivered electrical signal at a second electrode position, and determine a myocardial tissue displacement based at least in part on the sensed potential, wherein the circuitry is operative to diagnose a cardiac condition based at least in part on the displacement.

21. The system of claim 20 wherein the one or more implantable leads comprises at least two leads including a first lead that is configured for placement in a right ventricle and a second lead that is configured for placement in a left ventricle.

22. The system of claim 21 wherein the circuitry is operative to deliver an electrical signal to a first electrode carried by the first lead, and to sense a potential generated by the delivered electrical signal at a second electrode carried by the second lead.

* * * * *